(12) United States Patent
Bionda et al.

(10) Patent No.: US 11,357,523 B2
(45) Date of Patent: Jun. 14, 2022

(54) DEVICE AND METHOD FOR THE FRAGMENTATION OF A CALCULUS

(71) Applicant: FERTON HOLDING S.A., Delémont (CH)

(72) Inventors: Pierre-Alain Bionda, Lausanne (CH); Jean-Yves Girod, Gland (CH); Gary Evans, Allinges (FR)

(73) Assignee: FERTON HOLDING S.A., Delémont (CH)

( * ) Notice: Subject to any disclaimer, the term of this patent is extended or adjusted under 35 U.S.C. 154(b) by 0 days.

(21) Appl. No.: 16/963,437

(22) PCT Filed: Jan. 18, 2019

(86) PCT No.: PCT/EP2019/051283
§ 371 (c)(1),
(2) Date: Jul. 20, 2020

(87) PCT Pub. No.: WO2019/141822
PCT Pub. Date: Jul. 25, 2019

(65) Prior Publication Data
US 2021/0038238 A1 Feb. 11, 2021

(30) Foreign Application Priority Data
Jan. 19, 2018 (DE) .................... 10 2018 101 215.2

(51) Int. Cl.
*A61B 17/22* (2006.01)
*B06B 1/04* (2006.01)
(Continued)

(52) U.S. Cl.
CPC .......... *A61B 17/22012* (2013.01); *B06B 1/04* (2013.01); *B06B 1/0611* (2013.01);
(Continued)

(58) Field of Classification Search
CPC .......... A61B 17/2202; A61B 17/22012; A61B 17/32002; A61B 17/32053;
(Continued)

(56) References Cited

U.S. PATENT DOCUMENTS

2002/0010478 A1* 1/2002 Menne ............. A61B 17/22012
606/128
2004/0010267 A1 1/2004 Nakamura et al.
(Continued)

FOREIGN PATENT DOCUMENTS

CN 104473674 B 3/2017
DE 10029580 C1 1/2002
(Continued)

OTHER PUBLICATIONS

International Preliminary Report on Patentability dated Jul. 21, 2020 re: Application No. PCT/EP2019/051283, pp. 1-7, citing: US 2014/336665 A1, CN 104 473 674 B.
(Continued)

*Primary Examiner* — Robert A Lynch
(74) *Attorney, Agent, or Firm* — Cantor Colburn LLP

(57) ABSTRACT

A device for the fragmentation of a calculus includes a probe, and a drive unit for deflecting the probe along the longitudinal extension thereof. The drive unit includes a first drive element for periodically deflecting the probe and a second drive element for the pulsed deflection of the probe. The drive unit is configured such that periodic deflection and pulsed deflection can be superimposed.

7 Claims, 2 Drawing Sheets

(51) Int. Cl.
*B06B 1/06* (2006.01)
*A61B 17/32* (2006.01)

(52) U.S. Cl.
CPC .............. *A61B 2017/22011* (2013.01); *A61B 2017/22014* (2013.01); *A61B 2017/320088* (2013.01); *B06B 2201/76* (2013.01)

(58) Field of Classification Search
CPC ........ A61B 17/22011; A61B 17/22014; A61B 17/22015; A61B 17/22017; A61B 17/22018; A61B 17/22079; A61B 17/320028; A61B 17/32008; A61B 17/320088; A61B 17/32073; A61B 17/32007; B06B 2201/76; B06B 1/04; B06B 1/045; B06B 1/06; B06B 1/0603; B06B 1/0607; B06B 1/0611; B06B 1/0625; B06B 1/0633
See application file for complete search history.

(56) References Cited

U.S. PATENT DOCUMENTS

2004/0138594 A1\* 7/2004 Sekino et al. ........... A61H 1/00 601/4
2005/0209620 A1 9/2005 Du et al.
2014/0336665 A1\* 11/2014 Gavala et al. ... A61B 17/22012 606/128

FOREIGN PATENT DOCUMENTS

DE 102006021049 A1 11/2007
EP 1163884 B1 9/2009

OTHER PUBLICATIONS

International Search Report dated Apr. 8, 2019 re: Application No. PCT/EP2019/051283, pp. 1-3, citing: US2014336665 A1, CN104473674 B, US2005209620 A1, US 20040102667 A1 and DE 10029580 C1.

\* cited by examiner

DEVICE AND METHOD FOR THE FRAGMENTATION OF A CALCULUS

TECHNICAL FIELD

The present disclosure concerns a device and a method for breaking up a body stone.

BACKGROUND

For the removal of body stones, for example from body cavities, it is necessary to first crush them, whereby the crushing is carried out into small particles that can leave spontaneously or be flushed directly from the body. The crushing of the body stones is carried out, for example, by mechanical compressive and tensile stresses which are exerted on the body stones during intracorporal lithotripsy with a proximal end of a (metal) probe serving as a wave guide. Such tensions lead to fragments being spalled from the surface of the body stone and finally cause its fragmentation.

Well known are, for example, intracorporal lithotripters, in which the probe is excited to longitudinal oscillations by an electrically controlled ultrasound transducer. With a device of this type, the body stones can usually be broken up into very fine fragments.

Lithotripters are also known, in which the distal end of the probe is impacted by a pneumatically driven impact part. Such shock wave lithotripters, which in other embodiments may also have an electric drive of the impact part, allow higher maximum amplitudes or pulses of the probe tip, but are not optimally suited for very fine fragmentation. For example, a device is known from EP 1 163 884 B1 in which a special electrical drive of the ultrasonic transducer allows switching between a periodic vibration excitation of the probe and a pulse-shaped vibration excitation of the probe based on a voltage pulse. Furthermore, it is known from DE 100 29 580 C1 to switch between a first operating state in which a periodic deflection of the probe is caused and a second operating state in which a pulse-shaped deflection of the probe is caused.

The known devices have the disadvantage, however, that it is not possible with one and the same device to break both large and hard body stones, which requires a high maximum amplitude of the or a large impulse via the probe, and at the same time to enable very fine body stone fragmentation, which requires low amplitudes or deflections of the probe at very high frequencies.

SUMMARY

The present disclosure provides a device of the type mentioned above in such a way that a more flexible and efficient stone shattering can be carried out, taking into account the advantages and disadvantages of these known processes.

This is achieved by a device for breaking up a body stone according to claim 1 and by a method for breaking up a body stone according to claim 10. Further advantages and features result from the subclaims as well as the description and the attached figures.

According to the disclosure, a device for breaking up a body stone, in particular a lithotripter, is provided with a probe and a drive unit for deflecting the probe or for introducing an impact pulse into the probe along its longitudinal extension, the drive unit comprising a first drive device for periodic deflection of the probe and a second drive device for pulse-shaped deflection of the probe, the drive unit being designed in such a way that an effect device on the first drive device emanating from the second drive is reduced. By "deflection" the disclosure also means the introduction or transmission of a shock wave or impulse into or via the probe onto the body stone.

In contrast to the state of the art, the reduction of the effect of the second drive unit on the first drive unit according to the disclosure protects the first drive unit from damage during operation. Otherwise, such damage could be expected, at least in the long run, due to the intensive driving effect of the second drive unit on the probe, which is also noticeable or perceptible in the area of the first drive unit. As a result, it is no longer absolutely necessary, for example, to disconnect the second drive device from the drive unit mechanically and/or to disconnect contact with the probe in order to protect the first drive device, if only the second drive device is to be operated. In other words, it is not necessary to disconnect the first drive device from the second drive device and/or the probe, for example when switching between a first mode of operation in which only periodic deflection is initiated and a second mode of operation in which only pulse deflection is initiated. Furthermore, the design according to the disclosure even allows periodic and pulsed deflections to be realized simultaneously.

In principle, a design for reducing the effect of the second drive device means any measure on the drive unit which can reduce the effect on the first drive device. This means, for example, damping a pulse-shaped oscillation emanating from the second drive device and the associated forces before they enter the first drive device. This reduction can be determined, for example, by comparison with a drive unit in which the measure was not taken and/or an opposite measure was taken. It is conceivable here, for example, that the measure is used to damp a pulse-shaped vibration or compression wave excited by the second drive device, in particular in a force-transmitting oscillating part, by more than 50%, preferably more than 70% and more preferably more than 85% (relative to amplitude when introduced into the oscillating part) before it is coupled or introduced into the first drive device. Preferably, the measure serves to damp pulsed vibrations.

According to a preferred embodiment, it is intended that the drive unit is designed in such a way that the periodic deflection and the pulse-shaped deflection can be superimposed. In contrast to the devices known from the state of the art for breaking up body stones, it is thus possible to use the drive unit for the superimposition of periodic and pulse-shaped deflections. In other words: periodic and impulse-shaped deflections of the probe can be induced simultaneously, at least temporarily. During this, the first and the second drive device act on the probe simultaneously, i.e. the first and the second drive device are in operation simultaneously.

For example, it is not necessary to alternately connect the first drive device and the second drive device to the probe. It has been shown that with a deflection that has both a periodic and a pulsed component, the efficiency of the breaking up can be significantly increased to a degree that goes far beyond the successive application of both operating modes. The device according to an embodiment is designed to be able to change between a first operating mode, in which only the periodic deflection is initiated, and a second operating mode, in which only the pulsed deflection is initiated, as well as a third operating mode, in which the periodic and pulsed interpretation are superimposed, selectively or as required.

Basically, a periodic deflection is an oscillation, in particular an ultrasonic oscillation, which causes a standing wave in the probe, whereas a pulse-shaped deflection is, for example, a beating or hammering deflection. Preferably, a deflection caused by the second drive device is many times greater than the deflection caused by the first drive device. For example, the probe is needle-shaped and preferably hollow, with the needle-shaped form determining the longitudinal extension of the probe. This means that a deflection along the longitudinal extension corresponds to a translatory back and forth movement of the probe. Furthermore, it is particularly preferred that the probe is exchangeable or can be detachably connected to the drive unit. For example, the probe can be screwed to the drive unit via a thread.

Preferably, the first drive device and the second drive device are arranged offset to each other along a longitudinal axis which, in the mounted state of the probe, is parallel to its longitudinal extension, the second drive device in the drive unit being arranged closer to the probe than the first drive device. It is therefore advantageous that the force causing the pulse-shaped deflection does not have to be guided past the first drive device on its way to the probe. However, it is also conceivable that the first drive device is located closer to the probe than the second drive device. The first and second drive device each act on the probe by means of forces running parallel to the longitudinal axis in order to achieve the desired superimposition of the periodic and pulse-shaped deflection.

According to a preferred embodiment of the present disclosure, it is intended that the first drive device comprising piezoceramic elements acts on the probe via an oscillating part and/or the second drive device acts on the probe via a bumper. It is also conceivable that the second drive device acts directly on the probe. Preferably, the first drive device and the second drive device act on the probe separately or in isolation, i.e. not via a common force flow medium. This decoupling when the forces caused by the first drive device and the second drive device act on the probe proves to be advantageous, since a direct influence of the forces, which e.g. cause the pulsed oscillations, on the first drive device can be reduced. For example, the pulse-shaped oscillation emanating from the second drive device can only reach the first drive device via the thread. Preferably, the force from the second drive unit is applied directly to the probe, for example to a collar element of the probe, and not via the thread connecting the probe to the drive unit. This means that a force from the second drive device is directly introduced into the probe. Furthermore, it is preferable that the oscillating part is elastically supported in the drive unit to form a standing wave. In this case, the probe is preferably connected to the oscillating part in a non-positive and/or positive-locking manner. For example, the probe is screwed to the oscillating part, which means that a standing wave is formed in both the probe and the oscillating part when excited by the first drive device.

In a further embodiment of the present disclosure, it is provided that the first drive device transmits a force causing the periodic oscillation to the oscillating part via a transmission area, the transmission area being designed frequency-selectively, in particular as a low-pass filter, for damping pulse-shaped oscillations. This makes it possible in a beneficial manner for pulse-shaped oscillations, in particular those caused by the second drive device during simultaneous operation of the first and second drive devices and which find their path via the oscillating part to the first drive device, to be damped before they can penetrate into the first drive device. It is thus prevented that pulse-shaped oscillations, in particular pressure and force peaks, are fed into the first drive device without damping. As a result, damage to the first drive device can be counteracted, which would otherwise be expected if pulse-shaped oscillations were to be introduced into the first drive device all the time.

Frequency-selective design is understood to mean such design of the transmission range, for example by the shape and/or material of the transmission range, that oscillations of a certain frequency or frequency band are attenuated more than oscillations of another frequency or frequency band. The design as a low-pass filter proves to be particularly advantageous because the high-frequency oscillations resulting from the pulse-like oscillations of the impacts of the second drive unit are damped or even suppressed. For this reason, the frequency-selective design ensures the long-term functionality of the device, especially in spite of the loads caused by the simultaneous starting-up of the first and second drive units.

It is expedient that the transmission area between a transmission body of the first drive device and the oscillating part has a cross-sectional taper, for example in the form of a washer, whereby the effect, in particular force effect, of the second drive unit on the first drive unit is reduced. With the cross-sectional taper it can be ensured in an advantageous manner that the force or impulses for the periodic deflection or for the formation of the standing wave can be transmitted unhindered to the oscillating part, while a large portion of the impulse-shaped excitation is reflected at the cross-sectional taper and thus cannot be introduced into the first drive device.

By a cross-sectional taper, the expert understands in particular a cross-sectional area decreasing in the direction of the longitudinal axis, which serves to transmit the force emanating from the first drive direction to the vibrating part. The cross-sectional taper can be stepwise and it is also conceivable that the cross-sectional taper is multi-step. Furthermore, it is also conceivable that the transmission area in the assembled state is formed like a web, for example in the form of an annular web, between the first drive device and the oscillating part. The web can be interrupted or continuous in a plane perpendicular to the longitudinal axis.

It is particularly preferred if the transmission range is realized by a washer, which is, for example, clamped between the first drive device and the oscillating part in the mounted state or is connected to the first drive device in a non-positive or material-locking manner. For example, the web, viewed in a direction perpendicular to the longitudinal axis, is arranged substantially at the level of half the extension of the first drive device in the same direction. It is also conceivable that several webs are arranged in the transmission area, for example concentrically to each other.

Furthermore, it is preferable for the cross-sectional taper to take on a value between 0.02 and 0.5, preferably between 0.02 and 0.25 and more preferably between 0.02 and 0.1. Here, the cross-sectional taper is understood in particular to mean the reduction in area in the direction of the longitudinal axis. I.e. for quantitative indication of the cross-sectional taper, the cross-sectional taper is determined as the ratio of the first cross-section, dimensioned perpendicularly to the longitudinal axis, in the transmission area to a second cross-section, dimensioned perpendicularly to the longitudinal axis, of the first drive device, in particular at its end face facing the transmission area. In order to achieve a sufficient damping effect, the cross-sectional tapers between 0.02 and 0.1 have proven to be particularly advantageous. In this case, the transmission area is still wide enough so that the transmission area is not deformed or damaged in the long term due to the vibration load.

It is conceivable that the first drive device, viewed in the direction of the longitudinal axis, has a transmission area at each end, in particular with a cross-sectional taper. In particular, it is provided that the transmission area designed for frequency-selective transmission is formed on a side of the first drive device facing the second drive device, in particular an end face, or on an end face facing the probe. It has proven to be particularly advantageous if the transmission area is arranged exclusively on one of the end faces of the first drive device facing the probe or the second drive device.

It is preferably provided that an additional mass is provided between the first drive device and the second drive device, wherein preferably the oscillating part has a base body, wherein the oscillating part, in particular adjacent to the transmission area designed for frequency-selective transmission, has a projection projecting from the base body perpendicularly to the longitudinal axis. The introduction of the additional mass between the first drive device and the second drive device has proven to be an effective measure with which the effect of the second drive device on the first drive device can be further damped or reduced. The additional mass is preferably designed as an integral part of the oscillating part. It is conceivable that the cross-section of the oscillating part, which is dimensioned perpendicularly to the longitudinal axis, assumes more than 1.2 times, preferably more than 1.5 times and more preferably more than 1.8 times the cross-section of the oscillating part outside the projection. In particular, the projection forms a kind of driver by means of which the vibrating part is excited or moved for periodic vibration. Preferably, a ratio between a length of the projection measured in the direction of the longitudinal axis and a length or total length of the oscillating part measured in the direction of the longitudinal axis takes on a value between 0.1 and 0.5, preferably between 0.25 and 0.4 and more preferably between 0.28 and 0.38. This comparatively large dimensioning of the projection is advantageous in providing a larger mass through which the pulse-shaped vibration must pass before it can couple into the first drive device.

In a further embodiment it is intended that a hollow area in the probe and a hollow area in the oscillating part form a hollow channel, in particular a hollow channel without cross-sectional change, for sucking off body stone fragments. Preferably, the hollow area in the probe merges into the hollow area of the oscillating part without changing its cross-section. For this purpose, the oscillating part and the probe are designed in such a way that in the connected, in particular screwed-on state, the hollow area in the probe is aligned with the hollow area of the oscillating part. It is then advantageous to use the hollow channel to suck off shattered body stone fragments during operation.

It is expedient that the first drive device comprises at least one piezo element and/or the second drive device comprises at least one electromagnet, in particular in the form of an electric coil. In particular, several piezo elements stacked next to each other or stacked together form a piezo stack with which ultrasonic oscillations can be provided reliably in an advantageous way. However, the piezo elements are susceptible to breakage, in particular to impulsive oscillations introduced into the piezo stack. In this respect, the frequency-selective design of the transmission area proves to be particularly advantageous for the piezo elements, since the piezo elements, which are preferably made of a ceramic material, can thus be protected against breakage or other damage. By means of the second drive device, projectiles can be accelerated, preferably weighing between 10 and 100 g, and the projectile can be accelerated onto the bouncing body at a frequency between 1 and 30 Hz. Especially suitable frequencies are between 5 and 15 Hz. Impact velocities between 1 and 5 m/s are achieved. An anvil is preferably used as the bumper, which rests against the probe and transmits the impact impulse to the probe.

It is preferable that a transmission body, preferably a metallic transmission body, is provided between the transmission area and the piezo element. The transmission body forms a termination of the first drive device, in particular in the direction of the longitudinal axis. The transmission body ensures that the tapered cross-section of the transmission area does not directly adjoin a piezo element. Finally, a large and flat contact surface for the piezo element is required to prevent unintentional breakage of the piezo element. This contact surface can be provided with the transmission body, so that the tapered cross-section of the transmission area does not pose any danger to the piezo elements.

A further aspect of the present disclosure is a method of breaking up a body stone by means of a probe and a drive unit for deflecting the probe along its longitudinal axis, in particular by means of a device according to any one of the preceding claims, wherein the drive unit comprises a first drive device and a second drive device, the probe being deflected simultaneously by the first drive device and the second drive device. All features described for the device according to the disclosure and its advantages can also be transferred analogously to the method according to the disclosure and vice versa.

It is advisable for the device to include a hand instrument which has a housing within which the drive unit is located. It is also useful to have a supply unit, for example in the form of a stationary unit, which is connected to the hand instrument via supply lines for electricity, air and/or other media. It may also be advantageous for the stationary unit to be designed to change operating modes of the hand instrument or the like.

It goes without saying that operating modes and the like can also be adjusted on the hand instrument itself. It is an advantage for the probe to be accommodated with one end inside a guide tube or guide channel, over which a tip of the probe, i.e. its distal end, protrudes forward for the possibility of contact with a stone to be broken up. It is advisable that the guide tube is dimensioned so that an annular channel is formed between it and the probe, to which a suction pump can be connected. The annular channel thus forms a suction channel which, when the suction pump is connected, holds the stone at the end of the guide tube at the beginning of the stone breaking process so that the impact energy transmitted at the tip of the probe can have a precisely targeted effect on the stone. In addition, the ring channel can be used as a suction channel for stone fragments of a size smaller than the cross-section of the ring channel. Alternatively, preferably a hollow probe can also be arranged within the guide tube, whereby the probe itself then provides an suction channel. The decisive factor is that the drive unit is designed for a periodic and at the same time for a pulse-shaped deflection of the probe.

A particular advantage is that the impulse-shaped deflection is greater than the periodic deflection. Deflection refers to the distance or the maximum amplitude by which the probe or the probe tip moves back and forth. Thus, the advantages of a device with a pneumatically driven oscillating part and the advantages of a device with an electrically controlled ultrasonic transducer can be combined in one device by means of the drive unit according to the disclosure.

Advantageously, the piezo stack is essentially tubular, i.e. it has an opening or passage in the middle along its longitudinal axis. The aforementioned guide tube is located within the opening of the piezo stack, or the guide channel is defined by the opening, within which the oscillating part is located.

The longitudinal direction of the piezo stack therefore extends advantageously along the longitudinal axis of the device. It is advisable that the cross-section or the outer contour of the piezo stack transverse to the longitudinal direction or axial direction is essentially round, in particular essentially circular. Any other shapes are also conceivable, for example oval or angular designs. It goes without saying that the geometric features mentioned above apply in the same way to each of the piezo elements. A piezo element is basically a component that uses the piezoelectric effect to perform a mechanical movement by applying an electrical voltage, for example via two electrodes. The relative expansion or mechanical movement of the piezo element is proportional to the electric field strength, which is higher the smaller the distance between the two electrodes at a given voltage.

For multilayer piezo elements, i.e. piezo stacks, this is preferably achieved by a stacked arrangement with electrodes in between. A typical number of piezo elements is between two and eight slices, wherein in particular only an even number of slices is used. It is advantageous that the plus and minus electrodes are connected or electrically connected on the outside of the piezo stack. It is advantageous that the piezo stack or the piezo elements in the round or essentially circular version have an outer diameter of about 15 to 30 mm, preferably about 20 mm.

An inner diameter of the piezostack or the piezo elements preferably has an inner diameter of 5 to 10 mm, very preferably of about 8 to 9 mm. A thickness of the disk is preferably about 3 to 7 mm, very preferably about 4 to 6 mm. A particularly preferred version of the piezo stack comprises four (4) piezo elements, has an outer diameter of about 20 mm and an inner diameter of about 8.5 mm, wherein the thickness of a piezo element is preferably about 4 mm.

It is advisable to design the device in such a way that the piezo stack has a length of about 10 to 50 mm along the longitudinal axis. Preferably, the length is about 15 to 30 mm, more preferably about 15 to 18 mm. Tests have shown that an optimum periodic deflection of the probe can be achieved with a piezo stack of this length (in combination with the previously mentioned inner and outer diameters). It is advantageous that the piezo stack is enclosed by an insulating layer, which can simultaneously serve as a housing or housing element. It goes without saying that the piezo elements do not all have to be of the same thickness, but that the thicknesses of the piezo elements can preferably be of different designs. Piezoelements of different materials can also be preferred. This applies in the same way to the outer diameter and/or the inner diameter, which also need not be constant along the axial direction.

Preferably, the device is designed in such a way that during the periodic deflection the distal end of the probe performs an essentially sinusoidal movement in the direction of the longitudinal axis, which is designed for the breaking up of the body stone, and that a frequency of the periodic deflection is about 15 to 50 kHz, more preferably 25 kHz, and that the deflection of the distal end (peak to peak) of the probe in the longitudinal extension is in the range of about 5 to 100 μm.

Furthermore, the device is preferably designed in such a way that during the pulsed deflection at the distal end a pressure pulse is introduced which is designed to break up the body stone and that a frequency of the pulsed deflection is approximately 1 to 100 Hz, preferably between 1 to 30 Hz, and that the deflection of the distal end of the probe from the rest position in the axial direction is in a range of approximately 50 to 200 μm, preferably between 75 μm and 150 μm. In combined operation, i.e. when both drives are activated simultaneously, amplitudes from the rest position of 75 to 250 μm are preferably achieved, ideally amplitudes between 100 and 150 μm. It is therefore expedient for the periodic excitation to take place with a frequency that is orders of magnitude higher than the pulse-shaped deflection. It is advantageous that the periodic deflection or its frequency is in the range of known ultrasonic transducers. The deflection or the maximum amplitude of the probe in the case of the pulsed deflection is significantly higher than in the case of the periodic deflection. The advantage of the pulsed deflection is that it is in the range of pneumatically driven oscillating parts. A voltage can be applied through the electrodes attached to the piezo stack, thus creating an electric field.

The expansion of the piezo stack or the piezo elements depends among other things on the electric field strength. The magnitude of the applied voltage or the magnitude of the electric field can the deflection, i.e. the maximum amplitude. Basically, state of the art circuitry can be used to control the piezo stack or the piezo elements. These can be integrated into the hand instrument. However, they are particularly preferred as part of the stationary unit already mentioned.

Due to the high heat development of the first and second drive device, it is preferable to cool the hand instrument and/or the working unit, especially with liquid cooling. For this purpose, in a preferred embodiment, the hand instrument has cavities and liquid connections through which a suitable cooling liquid, such as water, can be passed. The cooling liquid can then be cooled in the hand instrument at a suitable point or it can be fed into the supply unit to cool down there. The cooling circuits are usually closed.

BRIEF DESCRIPTION OF THE DRAWINGS

Further advantages and features result from the following description of preferred embodiments of the device according to the disclosure and the probe according to the disclosure with reference to the attached figures. Individual features of the individual embodiments can be combined within the scope of the disclosure.

It is shown in.

DETAILED DESCRIPTION OF THE DRAWINGS

Figure 1:
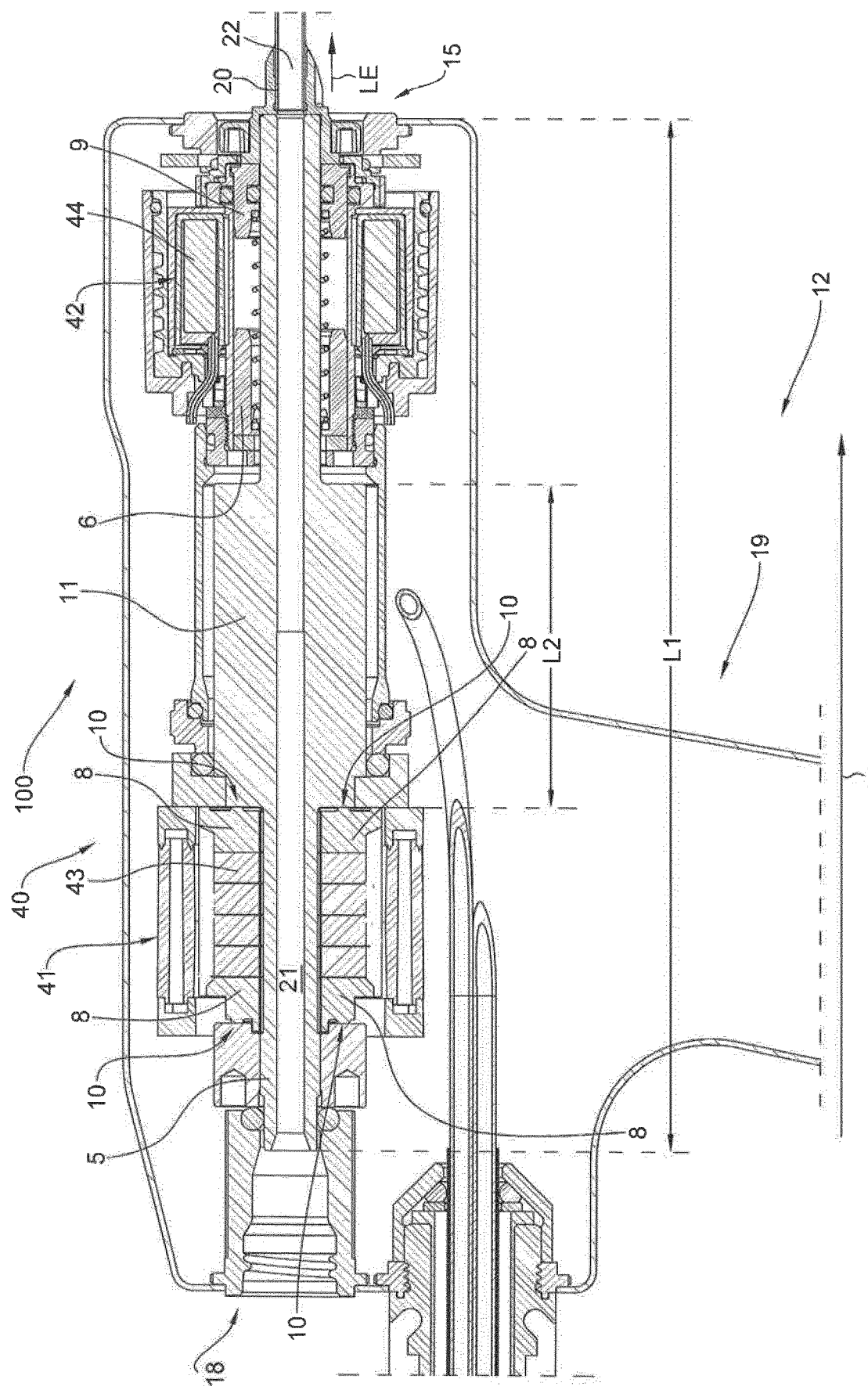
FIG. 1: a schematic representation of a preferred embodiment of a device for breaking up a body stone according to the present disclosure, and FIG. 2 a detailed view from FIG. 1.

FIG. 1 schematically illustrates a device 100 for the breaking up and/or removing body stones. For example, the body stones are kidney stones or urinary stones which can be broken up using the device 100. Essential components of such a device 100 are a needle-shaped and preferably hollow probe 20 and a drive unit 40 for deflecting the probe 20 along its longitudinal extension LE. In particular, it is provided that the excitations emanating from the drive unit 40 are transmitted to the probe 20, wherein a first proximal end of the probe 20 facing the body stone during operation, which is remote from the drive unit 40, causes the body stone or parts of the body stone to be broken up.

To change between different probe types, the probe 20 can be connected to the drive unit 40 in a detachable manner, preferably via an interface 15, for example by means of a thread. In the embodiment shown in FIG. 1, it is intended that the drive unit 40 is integrated into a hand-held device or hand instrument 12, in particular with an aspiration area 18, through which body stone fragments in particular can be aspirated, and a handle area 19. Furthermore, it is preferably provided that the drive unit 40 comprises a first drive device 41 for periodic deflection of the probe 20 and a second drive device 42 for pulse-shaped deflection of the probe 20. It is particularly preferably provided that the first drive device 41 acts on the probe 20 via an oscillating part 5 oscillating along a longitudinal axis LA and in so doing forms a standing wave, in particular in the oscillating part 5 and the probe 20. For the transmission of the oscillations, in particular ultrasonic oscillations, emanating from the first drive device 41, the oscillating part 5 and the probe 20 are arranged in alignment with one another in an operational state, viewed in the direction of the longitudinal axis LA, and lie against one another via their end faces, viewed in a direction running parallel to the longitudinal axis LA. In particular, one hollow area 21 of the oscillating part 5 and another hollow area 22 of the probe 2 are aligned with each other, for example, in order to be able to suck off or remove shattered or crushed fragments of body stones via the hollow area 21 and the other hollow area 22. Furthermore, it is conceivable that the drive unit 40 includes a cooling device (not shown) for its cooling.

Preferably, the first drive device 41 has a piezo stack, i.e. an arrangement of adjacent piezo elements 43. In particular, the stacked piezo elements 43 are designed as annular disks which surround the oscillating part 5 in a plane perpendicular to the longitudinal axis LA. For example, the stacked piezo elements 43 form part of a guide channel of the oscillating part 5 along the longitudinal axis LA. The oscillating part 5 passes through the stacked piezo elements, preferably in the middle. In particular, it is preferable that the oscillating part 5 is elastically supported in the drive unit 40 to form a standing wave. Furthermore, the oscillating part 5 comprises a projection 11 or driver projecting perpendicularly to the longitudinal axis LA from a base body, in particular an essentially rod-shaped base body. This projection 11 rests with one of its end or face sides, which delimit the projection 11 in the direction of the longitudinal axis LA, against a transmission area 10, which in turn is arranged in the direction of the longitudinal axis LA on the opposite side on the face side of the first drive device 41 (see FIG. 2). Via the transmission area 10 a force from the first drive device 41 is introduced or transmitted to the oscillating part 5 in order to cause a standing wave in the oscillating part 5 and thus also in the adjacent probe 20.

In addition to the first drive device 41, a second drive device 42 is provided for the pulse-shaped deflection of the probe 20. The second drive device 42 is arranged offset to that of the first drive device 41 as viewed in the direction of the longitudinal axis LA, the second drive device 42 preferably being arranged closer to the probe 20 than the first drive device 41. For example, the second drive device 42 is arranged at the end of the oscillating part section 18 facing the probe 20 and the first drive device 41 is arranged at the end of the oscillating part section 42 facing away from the probe 20. In particular, the projection 11 of the oscillating part 5, viewed in the direction of the longitudinal axis LA, is arranged between the first drive device 41 and the second drive device 42.

Preferably, the second drive device 42 comprises an electromagnet 44 which accelerates a projectile 6 along the longitudinal axis LA. The projectile 6 is preferably designed in the shape of an annular disk and—like the piezo elements 43—encases or surrounds the oscillating part 5 in a plane perpendicular to the longitudinal axis LA. During operation, the projectile 6 is accelerated onto a bumper 9, for example an anvil, and the bumper 9 then transmits the impact pulse, for example to a collar element of the probe 20. Preferably, the pulse-shaped deflection of the probe 20 is initiated by the second drive device 42 without using the oscillating part 5 of the first drive device 41 as a force flux or transmitter. In other words: To superimpose the periodic and the pulse-shaped deflection, the first drive device 41 and the second drive device 42 each act on the probe 20 without sharing a common force flux medium.

It has proved to be particularly advantageous for effective breaking up body stones if the periodic and the impulsive deflections of the probe 20 can be realized simultaneously, i.e. if the impulsive and the periodic deflections of the probe 20 are superimposed, i.e. impulsive and periodic deflections of the probe 20 are realized simultaneously. Due to the many times higher force effect of the second drive device 42 on the probe 20 compared to that of the first drive device 41, pulsed oscillations caused by the second drive device 41 may affect the first drive device 41. This is also the case if the first drive device 41 and the second drive device 42 do not cause the deflections of the probe 20 via a common force flux medium. In this case, the pulse-shaped oscillation reaches the first drive device 41 via the thread, for example.

Figure 2:
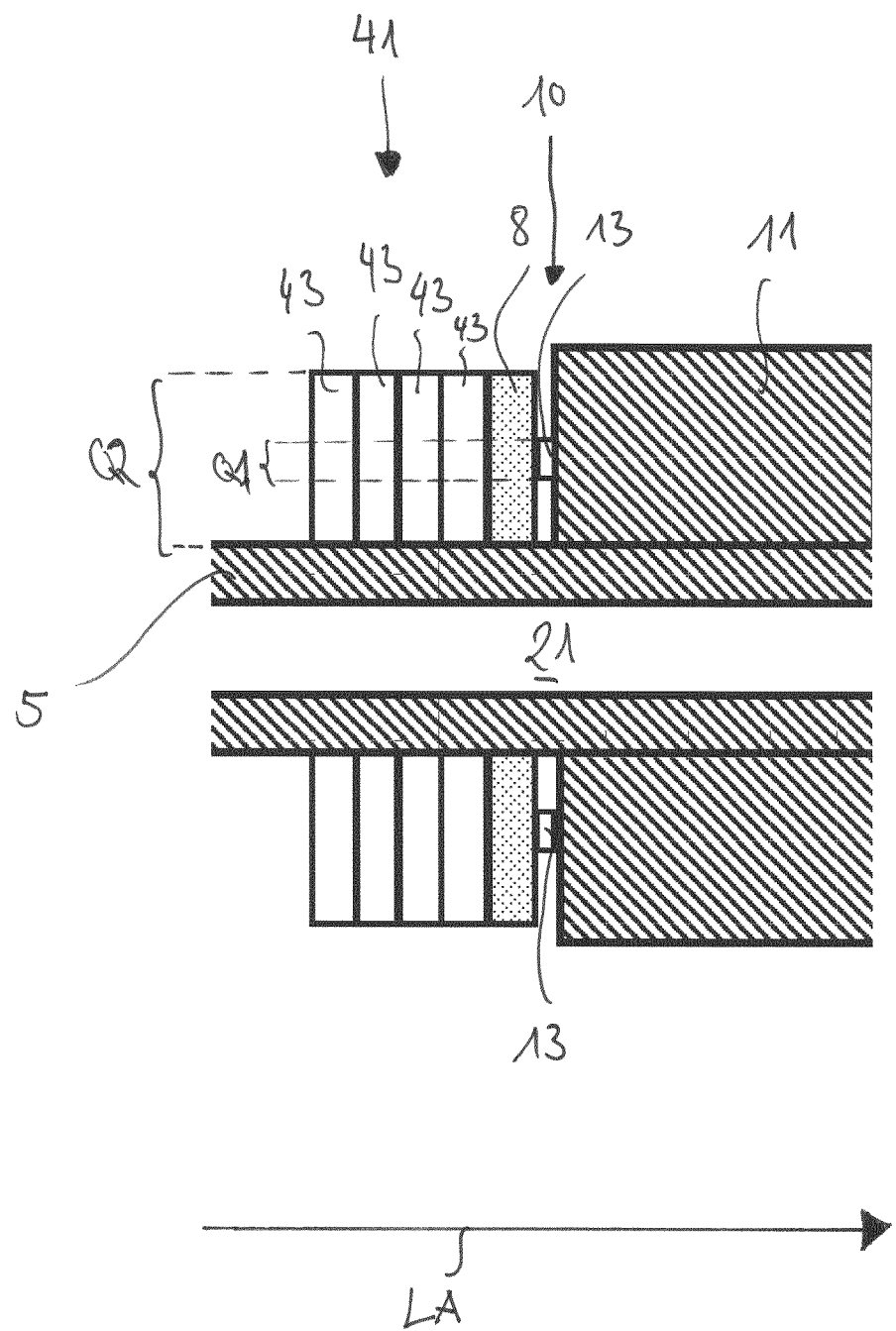

In order to counteract damage to the first drive device 41, it is provided that for decoupling from the second drive device 42, the transmission area 1 is designed for frequency-selective transmission of oscillations, in particular as a low-pass filter. In the embodiment shown, transmission the area 10 is designed as a cross-sectional projection or taper. FIG. 2 shows in detail the transmission area 10 between the first drive device 41 and the oscillating part 5, in particular the projection 11 of the oscillating part 5. A cross-sectional taper means in particular that a cross-section through which the force is transmitted changes, preferably becomes smaller, in the direction along which a force is transmitted from the first drive device to the oscillating part 5, i.e. along the longitudinal axis. In particular, the cross-sectional taper can be quantified by the ratio of the first cross-section Q1 dimensioned perpendicularly to the longitudinal axis in the transmission area 10 to a second cross-section Q2 dimensioned perpendicularly to the longitudinal axis LA of the first drive device 41, in particular at its end face facing the transmission area 10. The consequence of such a cross-sectional taper is a reflection of as large a proportion as possible of the pulsed oscillation which is caused by the second drive device 42 and would otherwise unintentionally be fed into the first drive device 41. This has the advantage of counteracting damage to the first drive device 41.

As an example, for decoupling from the second drive device 42, the transmission area 10 on the first drive device 41 can be designed as a web at the front (viewed in the direction of the longitudinal axis). It is conceivable that the web is closed or interrupted when viewed in the direction of rotation. It is also conceivable that for decoupling from the second drive device 42 a damping element, for example in the form of a washer 13, tuned to a resonant frequency of the first drive device 41, is arranged in the transmission area 10. For example, a washer 13 is arranged or clamped between the first drive device 41 and the oscillating part 5, via which the movements emanating from the first drive device 41 are transmitted to the oscillating part 5. For the purpose of designing the damping element to the resonant frequency of the first drive device, it is provided, for example, that a combination of elastic materials of different impedance is provided to form the washer 13. Furthermore, it is preferably provided that—in particular exclusively—the transmission area 10 facing the probe or the second drive device 42 is designed for the frequency-selective transmission of oscillations.

To further avoid damage to the piezo elements 43 of the first drive device, a transmission body 8 is provided between the piezo element 43 and the transmission area 10. The transmission body 8 is designed in such a way that it lies flat and with a large surface area against the piezo element 43. In other words, the transmission area 10 is not directly adjacent to the piezo element 43, since the cross-sectional taper provided in transmission area 10 would otherwise cause the piezo element 43 to break.

Furthermore, it is preferably provided that the movement or force emanating from the first drive device 41 is transmitted into an area of the oscillating part 5 by the oscillating part 5 having a projection 11 protruding perpendicular to the longitudinal axis LA adjacent to the transmission area 10 designed for frequency-selective transmission. Preferably a ratio between a length L2 of the projection 11 dimensioned in the direction of the longitudinal axis AL and a length L1 of the oscillating part 5 dimensioned in the direction of the longitudinal axis LA assumes a value between 0.1 and 0.5, preferably between 0.25 and 0.4 and more preferably between 0.28 and 0.38.

The invention claimed is:

1. A device for breaking up a body stone, comprising:
 a probe; and
 a drive unit for deflecting the probe along a longitudinal extension of the probe, wherein the drive unit comprises a first drive device for periodic deflection of the probe and a second drive device for pulse-shaped deflection of the probe, wherein the first drive device and the second drive device act on the same probe, wherein the drive unit is configured such that an effect on the first drive device emanating from the second drive device is reduced, wherein the first drive device acts on the probe via an oscillating part and the second drive device acts on the probe via a bumper and the first drive device transmits a force causing the periodic oscillation to the oscillating part via a transmission area, wherein the transmission area is configured frequency-selectively, as a low-pass filter, for damping pulse-shaped oscillations.

2. The device according to claim 1, wherein the drive unit is configured such that the periodic deflection and the pulse-shaped deflection is configured to be superimposed.

3. The device according to claim 1, wherein the transmission area between a transmission body of the first drive device and the oscillating part has a cross-sectional taper, whereby the effect, from the second drive unit to the first drive unit is reduced.

4. The device according to claim 1, wherein the transmission area designed for frequency-selective transmission is formed on a side of the first drive device facing the second drive device.

5. The device according to claim 1, wherein an additional mass is provided between the first drive device and the second drive device, wherein an oscillating part has a base body, wherein the oscillating part, has a projection projecting perpendicularly to the longitudinal axis.

6. The device according to claim 5, wherein a hollow area in the probe and a hollow area in the oscillating part form a hollow channel for sucking off body stone fragments.

7. The device according to claim 1, wherein the first drive device comprises a piezo element and/or the second drive device comprises an electromagnet.

* * * * *